United States Patent
Kvaale et al.

(10) Patent No.: US 8,496,910 B2
(45) Date of Patent: Jul. 30, 2013

(54) STABILISATION OF RADIOPHARMACEUTICAL PRECURSORS

(75) Inventors: Svein Kvaale, Oslo (NO); Dirk-Jan In t Veld, Oslo (NO); Torild Wickstrom, Oslo (NO)

(73) Assignee: GE Healthcare AS, Oslo (NO)

( * ) Notice: Subject to any disclaimer, the term of this patent is extended or adjusted under 35 U.S.C. 154(b) by 949 days.

(21) Appl. No.: 12/305,981

(22) PCT Filed: Jun. 20, 2007

(86) PCT No.: PCT/GB2007/002295
§ 371 (c)(1),
(2), (4) Date: Sep. 1, 2009

(87) PCT Pub. No.: WO2007/148083
PCT Pub. Date: Dec. 27, 2007

(65) Prior Publication Data
US 2010/0015052 A1 Jan. 21, 2010

Related U.S. Application Data

(60) Provisional application No. 60/805,386, filed on Jun. 21, 2006.

(51) Int. Cl.
*A61K 51/00* (2006.01)
*A61M 36/14* (2006.01)

(52) U.S. Cl.
USPC .................. 424/1.73; 424/1.11; 424/1.65

(58) Field of Classification Search
USPC ............... 424/1.11, 1.65, 1.73, 9.1; 536/27.1, 536/27.13, 27.21, 28.6, 29.1, 29.11, 29.13
See application file for complete search history.

(56) References Cited

U.S. PATENT DOCUMENTS

| 4,358,434 | A | * | 11/1982 | Tzodikov et al. | 424/1.65 |
| 5,843,396 | A | * | 12/1998 | Gan et al. | 424/1.41 |
| 6,630,477 | B1 | | 10/2003 | Daluge | |

FOREIGN PATENT DOCUMENTS

| EP | 0306597 | 11/1994 |
| EP | 1356827 | 10/2003 |
| WO | 99/26958 | 6/1999 |
| WO | 2004/043497 | 5/2004 |
| WO | 2006/067366 | 6/2006 |

OTHER PUBLICATIONS

Teng et al, Applied Radiation and Isotopes, (published online on Aug. 29, 2005), vol. 64, No. 2, pp. 187-193.*
Ponnamperuma et al (Science, 1965, vol. 148, No. 3674, pp. 1221-1223).*
Karwath, P. et.al. "Steam sterilization and automatic dispensing of [<18>F]fludeoxyglucose (FDG) for injection" Applied Radiation and Isotopes, Elsevier, Oxford, GB, vol. 62, No. 4, Apr. 2005, pp. 577-586.
Reischl, G. et.al. "Preparation of the hypoxia imaging PET tracer [<18>F]FAZA: reaction parameters and automation" Applied Radiation and Isotopes, Elsevier, Oxford, GB., vol. 62, No. 6 Jun. 2005 pp. 897-901.
Martin, S. et.al. "A new precursor for the radiosynthesis of [<18>F]FLT" Nuclear Medicine and Biology, Elsevier, NY, US, vol. 29, No. 2, Feb. 2002, pp. 263-273.
PCT/GB2007/002295 Int'l Search report/written opinion dated Jun. 2008.

* cited by examiner

*Primary Examiner* — D L Jones

(57) ABSTRACT

The invention relates to a method for improving stability of radiopharmaceutical precursors, and in particular non radiolabelled nucleoside derivatives which are used as precursors for production of radiolabelled nucleoside derivatives for use in in vivo imaging procedures such as positron emission tomography (PET). The invention further includes formulations of radiopharmaceutical precursors, and cassettes for automated synthesis apparatus comprising the same.

8 Claims, No Drawings

STABILISATION OF RADIOPHARMACEUTICAL PRECURSORS

This application is a filing under 35 U.S.C. 371 of international application number PCT/GB2007/002295, filed Jun. 20, 2007, which claims priority to application No. 60/805,386 filed Jun. 21, 2006, in The United States the entire disclosure of which is hereby incorporated by reference.

The present invention relates to a method for improving stability of radiopharmaceutical precursors, and in particular non radiolabelled nucleoside derivatives which are used as precursors for production of radiolabelled nucleoside derivatives for use in in vivo imaging procedures such as positron emission tomography (PET). The invention further includes formulations of radiopharmaceutical precursors, and cassettes for automated synthesis apparatus comprising the same.

Non radiolabelled nucleoside derivatives such as precursors for radiosynthesis of [$^{18}$F]fluorothymidine ([$^{18}$F]FLT) are currently supplied commercially as dry powders in dark glass vials flushed with inert gas and are advantageously stored at sub-ambient temperatures to ensure stability over a reasonable period. In the context of an automated radiosynthesis system such as TracerLab MX (Coincidence Technologies), this means that the non radiolabelled nucleoside derivative has to be stored separately from the other reagents and assembled into the cassette by the operator prior to running the radiolabelling process. Therefore, there exists the need for a method to improve stability of non radiolabelled nucleoside derivatives such as precursors for the radiosynthesis of [$^{18}$F] FLT to improve shelf-life and preferably allow storage at ambient temperature, for example, in the same package as the other reagents or as part of a preassembled cassette.

The present invention presents that by storing a non radiolabelled nucleoside derivative, such as a precursor for radiosynthesis of [$^{18}$F]FLT in an organic solvent rather than as a dry powder, the stability is improved. This runs contrary to expectations as normally degradation would be expected to occur more quickly in solution. Presentation of a non radiolabelled nucleoside derivative, such as a precursor for radiosynthesis of [$^{18}$F]FLT in an organic solvent has the further advantage that, being already in solution, dissolution of the non radiolabelled nucleoside derivative prior to performing radiolabelling can be avoided which may be particularly advantageous in an automated radiochemistry operation.

Therefore, according to one aspect of the invention, there is provided a method for improving stability of a radiopharmaceutical precursor, suitably a non radiolabelled nucleoside derivative which comprises storage of said radiopharmaceutical precursor in a solvent in a sealed container.

The term "radiopharmaceutical precursor" as used herein means a compound which may be radiolabelled, suitably with [$^{18}$F]fluorine or [$^{11}$C]carbon to prepare a radiolabelled PET tracer, provided that the radiopharmaceutical precursor is not a non fluoridated sugar derivative as defined below. In one aspect of the invention, the radiopharmaceutical precursor is a non radiolabelled nucleoside derivative as defined below.

The term "non radiolabelled nucleoside derivative" means a nucleoside derivative suitable for use as a precursor in synthesis of a $^{11}$C- or $^{18}$F-radiolabelled nucleoside derivative for PET imaging, for example a nucleoside derivative in which one of the OH groups is replaced by a leaving group and any other OH or amine groups are each optionally protected with a suitable protecting group. Such non radiolabelled nucleoside derivatives are suitably derivatives of thymine, cytosine, or uracil, most suitably thymine derivatives. In one aspect of the invention, the non radiolabelled nucleoside derivative is an [$^{18}$F]FLT Precursor. The term "[$^{18}$F]FLT Precursor" means a precursor compound suitable for radiolabelling with $^{18}$F to prepare [$^{18}$F]FLT. One class of [$^{18}$F]FLT Precursor used in the invention are those of formula (I):

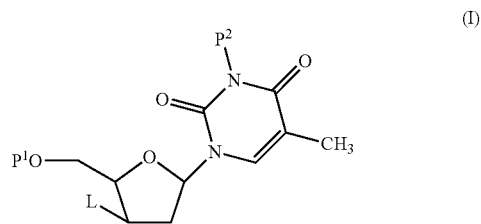

(I)

wherein L is a leaving group and P$^1$ and P$^2$ are each a suitable protecting group or hydrogen.

Suitable protecting groups which may be present in the non radiolabelled nucleotide derivatives are well known in the art and are described, for example, in "Protecting Groups in Organic Synthesis", Theodora W. Greene and Peter G. M. Wuts, published by John Wiley & Sons Inc. The particular protecting group will depend upon the intended process for preparation of the radiolabelled product but, for example, any hydroxy groups may be protected by conversion to alkyl or aromatic esters, for example by reaction with an alkanoyl chloride such as acetyl chloride. Alternatively, hydroxy groups may be converted to ethers, for example alkyl or benzyl ethers. In formula (I), suitably P$^1$ is selected from hydrogen, triphenylmethyl, tri-C$_{1-6}$alkylmethyl, triphenylsilyl, phenylcarbonyl, and tri-C$_{1-6}$alkylsilyl wherein any phenyl groups are optionally substituted by 1 to 5 substituents independently selected from C$_{1-6}$alkyl, C$_{1-6}$alkoxy, and halo, for example P$^1$ can be dimethoxytrityl or benzoyl. In formula (I) P$^2$ is suitably selected from hydrogen, a C$_{2-10}$alkyloxycarbonyl group such as tert-butoxycarbonyl ("Boc"), benzyl optionally substituted by 1 to 5 substituents independently selected from C$_{1-6}$alkyl, C$_{1-6}$alkoxy, and halo for example dimethoxybenzyl.

Suitable leaving groups L in the non radiolabelled nucleoside derivative and in formula (I) are also well known in the art and include halo such as iodo, arylsulphonates, such as toluene sulfonate, halo C$_{1-6}$alkylsulphonates, and C$_{1-6}$alkylsulphonates such as methane sulfonate. It is particularly preferred, however, that the leaving group is a trifluoromethane sulfonate (triflate) group or nitrophenylsulphonate (nosyl) group.

A further class of [$^{18}$F]FLT Precursor used in the invention are those of formula (Ia):

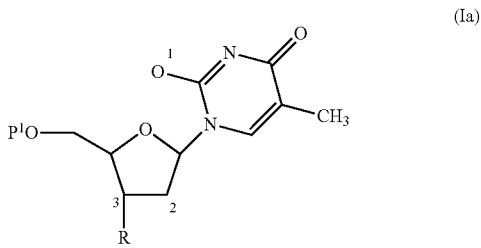

(Ia)

wherein P$^1$ is a suitable protecting group or hydrogen as described for the compound of formula (I); the thymine oxygen-1 is bonded to either carbon-3 (in which case R is hydrogen) or carbon-2 (in which case R is hydroxy).

The [$^{18}$F]FLT Precursor is suitably selected from:
1-[5-O-(4,4'-dimethoxytrityl)-2-deoxy-β-D-threo-pentofuranosyl]thymine;
2,2'-anhydro-(1-3-D-arabinofuranosyl)-5-methyluracil;
3'-deoxy-3'-iodothymidine;
3-N-Boc-1-[5-O-(4,4'-dimethoxytrityl)-3-O-nitrophenylsulfonyl-2-deoxy-β-D-lyxofuranosyl]thymidine, "Boc-FLT";
5'-O-(4,4'-dimethoxytrityl)-2,3'-anhydrothymidine;
5'-O-benzoyl-2,3'-anhydrothymidine;
5'-O-(4,4'-dimethoxytrityl)-2,3'-anhydrothymidine;
1-[5-O-(4,4'-dimethoxytrityl)-3-O-nitrophenylsulfonyl-2-deoxy-β-D-lyxofuranosyl]thymidine, "Non-Boc-FLT"; and
3-N-(2,4-dimethoxybenzyl)-1-[5-O-(4,4'-dimethoxytrityl)-3-O-nitrophenylsulfonyl-2-deoxy-β-D-lyxofuranosyl]thymidine. All of which are commercially available, for example from ABX GmbH (Germany).

A particularly well known non radiolabelled nucleoside derivative is 3-N-Boc-1-[5-O-(4,4'-dimethoxytrityl)-3-O-nitrophenylsulfonyl-2-deoxy-β-D-lyxofuranosyl]thymidine, which is commercially available and used as an [$^{18}$F]FLT Precursor.

The solvent used in the method may be an aprotic solvent (as defined more fully below) or a protic solvent. Suitable protic solvents include $C_{1-8}$alcohols, for example methanol, ethanol, isopropanol, isobutanol, acetone or octanol. The solvent used may be dry, meaning having a water content of 10000 ppm or less, suitably 1000 ppm or less, more suitably less than 600 ppm, and preferably less than 100 ppm.

In one aspect of the invention, it is advantageous that the radiopharmaceutical precursor is stored in the same solvent which will be used subsequently in the radiolabelling reaction. This avoids an extra step of solvent removal before radiolabelling. Therefore, according to a further aspect of the invention, there is provided a method for improving stability of a radiopharmaceutical precursor, suitably a non radiolabelled nucleoside derivative which comprises storage of said radiopharmaceutical precursor in an aprotic solvent in a sealed container.

Suitable aprotic solvents for this purpose include acetonitrile, dimethylformamide, dimethylsulfoxide, tetrahydrofuran, dioxan, 1,2-dimethoxyethane, sulfolane and N-methylpyrrolidinone. However, acetonitrile has been found to be a particularly suitable solvent for storage. The aprotic solvent used may be dry, meaning having a water content of 1000 ppm or less, suitably less than 600 ppm, and preferably less than 100 ppm. In an alternative embodiment of the invention, the aprotic solvent used may have a water content of between 1000 ppm and 50000 ppm, suitably a water content of 1000 ppm to 15000 ppm, more suitably 1500 ppm to 7000 ppm or 1800 ppm to 7000 ppm, and more suitably 1500 ppm to 7000 ppm or 1800 ppm to 2500 ppm. Using an aprotic solvent with such a controlled water content has the added advantage that the radiopharmaceutical precursor, suitably the non radiolabelled nucleoside derivative, may be presented in solution having the optimum water content for performing a subsequent radiolabelling reaction, thus avoiding the need to adjust the water content, for example by a drying step or by addition of further water or solvent.

As used herein, the term "ppm", when describing water content of a given solvent, means μgram water/gram.

Suitably, the radiopharmaceutical precursor, suitably the non radiolabelled nucleoside derivative is present in the solvent, suitably an aprotic solvent at a concentration suited for performing a subsequent radiolabelling reaction, for example from 0.1 mg/ml to 50 mg/ml, more suitably 5 mg/ml to 25 mg/ml, even more suitably 10 mg/ml to 18 mg/ml. In one particular embodiment, the non radiolabelled nucleoside derivative is present in the solvent, suitably an aprotic solvent at a concentration of 15 mg/ml. In a further embodiment, the non radiolabelled nucleoside derivative is present in the solvent, suitably an aprotic solvent at a concentration of 17.5 to 21.5 mg/ml.

Suitable sealed containers are those which do not interact with the solvent or with the radiopharmaceutical precursor, optionally permit maintenance of sterile integrity, plus optionally an inert headspace gas (e.g. nitrogen or argon), whilst also optionally permitting addition and withdrawal of solutions by syringe. Such containers include liquid-tight or gas-tight jars, flasks, ampoules and vials, the seal being provided by a liquid-tight or gas-tight closure such as a lid, stopper, or septum. A preferred such container is a septum-sealed vial, wherein the gas-tight closure is crimped on with an overseal (typically of aluminium). Such containers have the additional advantage that the closure can withstand vacuum if desired for example to change the headspace gas or degas solutions and can withstand an overpressured, for example to aid in the removal of the solution from the container.

Using the methods described herein, the radiopharmaceutical precursor, suitably the non radiolabelled nucleoside derivative, may be stored for extended periods of 2 days or more, for example up to 18 months, suitably up to 6 months, more suitably for up to 8 weeks, at temperatures at or below ambient, for example at −10° C. to 35° C., suitably 10° C. to 35° C. As mentioned above, storage at ambient temperature is particularly convenient.

In the alternative, there is provided a formulation of a radiopharmaceutical precursor, suitably a non radiolabelled nucleoside derivative, comprising said radiopharmaceutical precursor, and a solvent in a sealed container as described hereinbefore. The solvent present in the formulation may be an aprotic solvent or a protic solvent as described above.

In the alternative, there is further provided a formulation of a radiopharmaceutical precursor, suitably a non radiolabelled nucleoside derivative comprising said radiopharmaceutical precursor, and an aprotic solvent in a sealed container as described hereinbefore.

In the present specification, the term "non fluoridated sugar derivative" means a polysaccharide, oligosaccharide, disaccharide or monosaccharide sugar in which one of the OH groups is replaced by a leaving group and the other OH groups of the sugar are each optionally protected with a suitable protecting group. Such non fluoridated sugar derivatives include derivatives of monosaccharides such as glucose, fructose, ribose, arabinose, mannose or galactose; for example those of formula (II):

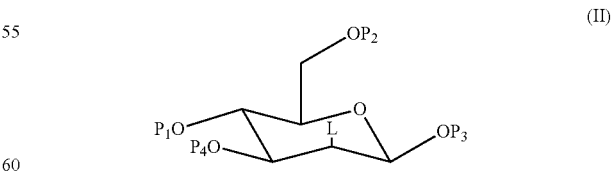

wherein L is a leaving group and $P_1$ to $P_4$ are each a suitable protecting group.

Suitable protecting groups which may be present in the non fluoridated sugar derivatives of formula (II) are well known in the art and are described, for example, in "Protecting Groups in Organic Synthesis", Theodora W. Greene and Peter G. M.

Wuts, published by John Wiley & Sons Inc. The particular protecting group will depend upon the intended process for preparation of the fluoridated product but, for example, the hydroxy groups may be protected by conversion to alkyl or aromatic esters, for example by reaction with an alkanoyl chloride such as acetyl chloride. Alternatively, hydroxy groups may be converted to ethers, for example alkyl or benzyl ethers. Suitably, the protecting groups $P_1$ to $P_4$ are each an acyl group.

Suitable leaving groups in the compounds of formula (II) are also well known in the art and include arylsulphonates such as toluene sulfonate, haloalkylsulphonates, and alkylsulphonates such as methane sulfonate. It is particularly preferred, however, that the leaving group is a trifluoromethane sulfonate (triflate) group.

A particularly well known non fluoridated sugar derivative is 1,3,4,6-tetra-O-acetyl-2-O-trifluoromethanesulfonyl-β-D-mannopyranose, commonly referred to as "mannose triflate". Mannose triflate is a commercially available non fluoridated sugar derivative which is used as a precursor for synthesis of 2-[$^{18}$F]fluoro-D-glucose ([$^{18}$F]FDG) via the protected intermediate 2-fluoro-1,3,4,6-tetra-O-acetyl-D-glucose (tetraacetylfluorodeoxyglucose or pFDG).

As would be apparent to a person skilled in the art, a formulation according to the invention may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid). And such ingredients may be added as part of a method according to the invention. However, presence of such ingredients is avoided where possible so that the radiolabelled nucleoside derivative may be produced in as pure a form as possible for subsequent use in an in-vivo imaging procedure. Therefore, formulations and methods as described herein in which the non radiolabelled nucleoside derivative and solvent are present in the sealed container without further ingredients.

Radiotracers, such as [$^{18}$F]FDG and [$^{18}$F]FLT are now often prepared on an automated radiosynthesis apparatus using nucleophilic radiofluoridation chemistry with $^{18}$F, based on the reagent Kryptofix™ 2.2.2. There are several examples of such apparatus commercially available, including Tracerlab MX (Coincidence Technologies SA) and Tracerlab FX (Nuclear Interface GmbH). Such apparatus commonly comprises a cassette, often disposable, in which the radiochemistry is performed, which is fitted to the apparatus in order to perform a radiosynthesis.

The cassette normally includes fluid pathways, a reaction vessel, and ports for receiving reagent vials as well as any solid-phase extraction cartridges used in post-radiosynthetic clean up steps.

A formulation of a radiopharmaceutical precursor, suitably a non radiolabelled nucleoside derivative as described herein may be housed in a disposable or removable cassette designed for use with the automated synthesis apparatus. Therefore, the invention further provides a cassette for an automated synthesis apparatus comprising a formulation of a non radiolabelled nucleoside derivative comprising said non radiolabelled nucleoside derivative, and a solvent in a sealed container as described hereinbefore. As demonstrated herein, the improved stability of the non radiolabelled nucleoside derivative when stored as a formulation according to the invention means that the cassette can be provided complete with all of the reagents required for the radiolabelling reaction, except for the radioisotope, and the cassette can be stored at ambient temperature thus avoiding the need for refrigeration.

The invention is illustrated by way of the examples below, in which the following abbreviations are used:
PET Precursor: 5'-O-dimethoxytrityl-2'-deoxy-3'-O-nosyl-β-D-threo-pentofuranosyl)-3-N-tert-butoxycarbonyl-thymine
HPLC: high performance liquid chromatography
IR: infrared spectrometry
UV: ultraviolet
RCP: radiochemical purity
MeCN: acetonitrile
Materials:
Vials: Fiolax 5 ml Glass vials (13 mm), Munnerstæaedter.
Stoppers: West 4432/50 gray 13 mm, Teflon coated.
Caps: Helvoet Pharma

EXPERIMENTAL 10 mg PET Precursor is weighed into each glass vial and dissolved in 100 μl dry acetonitrile to yield an acetonitrile solution.

Control samples of PET Precursor (without solvent) under air and under nitrogen are also prepared.

Filled and capped vials are kept in storage at 25° C. and 50° C. in thermally controlled cabinets for set periods of time at which "pull points" a vial is removed from storage and subjected to the testing outlined below.
Test Methods Used:
Non-radioactive methods (cold) performed:
Appearance/organoleptic test, all pull points
Purity by HPLC-UV, all pull points
NMR, all pull points
HPLC Method: octadecylsilyl silica gel (5 μm) column (Hichrom Nucleosil 100-5C18), temperature 25° C.; injection volume 20 μl; mobile phase of water acetonitrile gradient, 1 ml/min. Detection by spectrophotometer at 220 nm Results from radiolabelling with $^{18}$F in a glassy carbon reactor using the method described below are recorded (all pull points).

EXAMPLE 2

Stability of PET Precursor in Acetonitrile/Water

Using similar method to Example 1, the stability of PET Precursor in acetonitrile with water at level of approximately 725, 1450, and 2500 ppm is evaluated.

COMPARATIVE EXAMPLE

Stability of Dry Powder PET Precursor

Dry powder PET Precursor is stored in vials at different temperatures and for different time periods.

Results from radiolabelling in the glassy carbon reactor at time zero and after storage for different periods at 50° C. are recorded.
Radiolabelling Method The fluoride solution (200 μL in O-18 enriched water, 95%) is transferred to the glassy carbon reaction vessel. 12 mg Kryptofix (in 500 μl MeCN) and 100 μl of 0.1M potassium carbonate are added to the reaction vessel and dried by heating for 15 mins at 100° C. During the drying process $N_2$ is passed through the reaction vessel at 0.1 L/min and two 1 ml aliquots of MeCN are added to the reaction vessel at 5 and 10 minutes heating to aid azeotropic drying. The dried fluoride is cooled while maintaining the $N_2$ flow. 10 mg of 3-N-Boc-1-[5-O-(4,4'-dimethoxytrityl)-3-O-nitrophenylsulfonyl-2-deoxy-β-D-lyxofuranosyl]thymidine in 1 ml MeCN is transferred to the reaction vessel and heated at 130° C. for 5 minutes. After cooling, is 0.25 mL 1M HCl is added and heated @ 100° C. for 5 minutes. After cooling neutralise using 1.5 mL 2M NaOAc.

What is claimed is:

1. A method for improving stability of a non radiolabelled nucleoside derivative which comprises storage of a formulation of a non radiolabelled nucleoside derivative of formula (I):

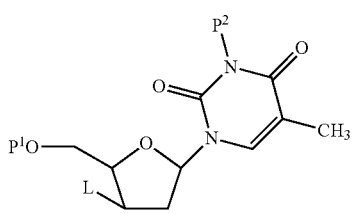
(I)

wherein $P^1$ is selected from the group consisting of hydrogen, triphenylmethyl, tri-$C_{1-6}$ alkylmethyl, triphensilyl, phenyl carbonyl, and tri-$C_{1-6}$ alkylsilyl wherein phenyl groups are optionally substituted by one to five substituents independently selected from the group consisting of $C_{1-6}$ alkyl, $C_{1-6}$ alkoxy, and halogen;

$P^2$ is selected from the group consisting of hydrogen, $C_{2-10}$ alkyloxycarbonyl, and benzyl optionally substituted with one to five substituents independently selected form $C_{1-6}$ alkyl, $C_{1-6}$ alkoxy, and halogen; and L is selected from the group consisting of halogen, arylsulphonate, halo $C_{1-6}$ alkyl sulphonate, and $C_{1-6}$ alkyl sulphonate and wherein said formulation consists essentially of said non radiolabelled nucleoside derivative, and a solvent in a sealed container and wherein the solvent has a water content of 1000 ppm or less.

2. A method according to claim 1 wherein the solvent is an aprotic solvent.

3. A method according to claim 1 wherein the solvent has a water content of less than 600 ppm.

4. A method according to claim 1 wherein the sealed container is a septum-sealed vial.

5. A formulation of a non radiolabelled nucleoside derivative of formula (I):

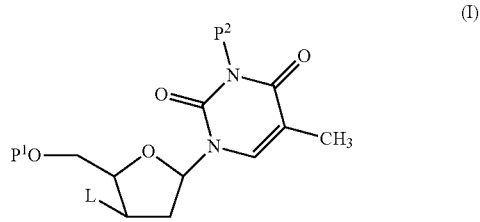
(I)

wherein $P^1$ is selected from the group consisting of hydrogen, triphenylmethyl, tri-$C_{1-6}$ alkylmethyl, triphensilyl, phenyl carbonyl, and tri-$C_{1-6}$ alkylsilyl wherein phenyl groups are optionally substituted by one to five substituents independently selected from the group consisting of $C_{1-6}$ alkyl, $C_{1-6}$ alkoxy, and halogen;

$P^2$ is selected from the group consisting of hydrogen, $C_{2-10}$ alkyloxycarbonyl, and benzyl optionally substituted with one to five substituents independently selected form $C_{1-6}$ alkyl, $C_{1-6}$ alkoxy, and halogen; and L is selected from the group consisting of halogen, arylsulphonate, halo $C_{1-6}$ alkyl sulphonate, and $C_{1-6}$ alkyl sulphonate and wherein said formulation consists essentially of said non radiolabelled nucleoside derivative, and a solvent in a sealed container and wherein the solvent has a water content of 1000 ppm or less.

6. A formulation according to claim 5 wherein the solvent is an aprotic solvent.

7. A formulation according to claim 5 wherein the solvent has a water content of less than 600 ppm.

8. A formulation according to claim 5 wherein the sealed container is a septum-sealed vial.

* * * * *